United States Patent [19]

Tunemoto et al.

[11] Patent Number: 4,749,407

[45] Date of Patent: Jun. 7, 1988

[54] N-PROPARGYL-N-(2-TRIFLUOROMETHYL-BENZOYL)-3-SUBSTITUTED BENZENESULFONAMIDE AND SELECTIVE HERBICIDE CONTAINING THE SAME AS AN ACTIVE INGREDIENT

[75] Inventors: Daiei Tunemoto, Zama; Hideko Sakai, Yokohama; Kiyosi Kondo, Yamato; Kaoru Mori, Kamifukuoka; Masahiro Watanabe, Sayama; Takeo Komata, Kamifukuoka; Kenji Motojima, Kakegawa, all of Japan

[73] Assignees: Sagami Chemical Research Center, Tokyo; Central Glass Co, Ltd., Ube, both of Japan

[21] Appl. No.: 877,380

[22] Filed: Jun. 23, 1986

[51] Int. Cl.$^4$ .................... A01N 9/16; C07C 143/78
[52] U.S. Cl. ......................... 71/103; 564/89; 564/90
[58] Field of Search ............... 71/103; 564/89, 90

[56] References Cited

U.S. PATENT DOCUMENTS 4,157,257  6/1979  Takematsu et al. ............ 564/89
4,233,061 11/1980  Takematsu et al. ............ 71/103

FOREIGN PATENT DOCUMENTS 53-44543  4/1978  Japan.
54-27535  3/1979  Japan.
116663    6/1985  Japan ............ 71/103

Primary Examiner—Anton H. Sutto
Attorney, Agent, or Firm—Foley & Lardner, Schwartz, Jeffery, Schwaab, Mack, Blumenthal & Evans

[57] ABSTRACT

There are disclosed an N-propargyl-N-(2-trifluoromethylbenzoyl)-3-substituted benzenesulfonamide represented by the general formula:

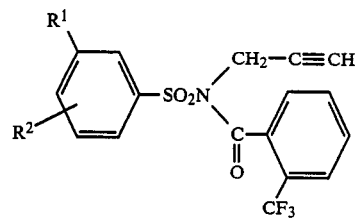

wherein $R^1$ represents a halogen atom, a lower alkyl group, a lower alkoxy group, a perfluoro-lower alkyl group having 1 to 4 carbon atoms, a nitro group, a cyano group, a carboxyl group or a lower alkoxycarbonyl group; and $R^2$ represents a hydrogen atom, a halogen atom, a lower alkyl group, a perfluoro-lower alkyl group having 1 to 4 carbon atoms, a lower alkoxy group, a nitro group, a cyano group, a carboxyl group or a lower alkoxycarbonyl group, and a selective herbicide containing the same as an active ingredient.

6 Claims, 1 Drawing Sheet

N-PROPARGYL-N-(2-TRIFLUOROMETHYLBEN-ZOYL)-3-SUBSTITUTED BENZENESULFONAMIDE AND SELECTIVE HERBICIDE CONTAINING THE SAME AS AN ACTIVE INGREDIENT

BACKGROUND OF THE INVENTION

This invention relates to a novel N-propargyl-N-(2-trifluoromethylbenzoyl)-3-substituted benzenesulfonamide and a selective herbicide containing the same as an active ingredient.

SUMMARY OF THE INVENTION

More specifically, this invention relates to a compound represented by the general formula (1):

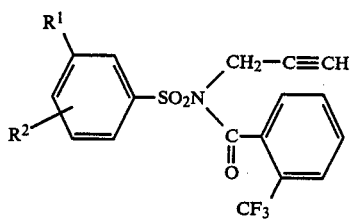

wherein $R^1$ represents a halogen atom, a lower alkyl group, a lower alkoxy group, a perfluoro-lower alkyl group having 1 to 4 carbon atoms, a nitro group, a cyano group, a carboxyl group or a lower alkoxycarbonyl group; and $R^2$ represents a hydrogen atom, a halogen atom, a lower alkyl group, a perfluoro-lower alkyl group having 1 to 4 carbon atoms, a lower alkoxy group, a nitro group, a cyano group, a carboxyl group or a lower alkoxycarbonyl group, and a selective herbicide containing the same as an active ingredient.

Heretofore, a large number of herbicides have been developed and used in practice. However, appearance of herbicides more improved in the points of herbicidal effects and the like have been desired. The present inventors have earnestly investigated in order to reply to such desires and have found that compounds represented by the general formula (1) exhibit excellent herbicidal effects.

PREFERRED EMBODIMENTS OF THE INVENTION

Figure 1:
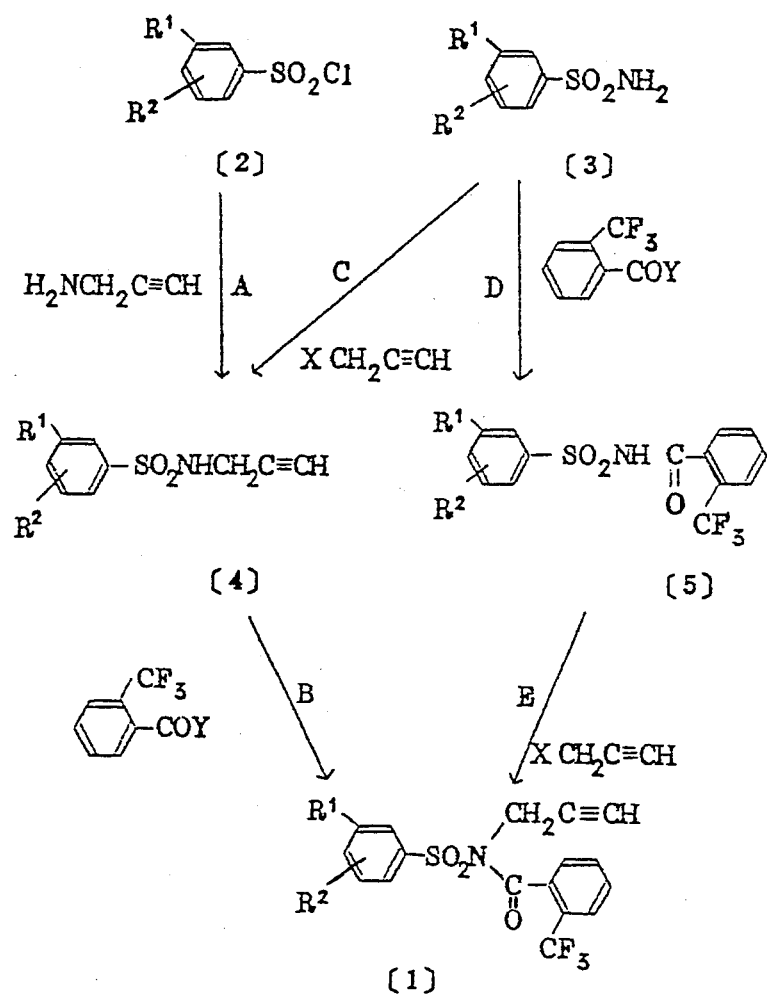
FIG. 1. shows reaction processes for preparing compounds according to the present invention.

The compounds represented by the general formula (1) have significant activities against annual weeds in a paddy field such as *Echinochola oryzicola, Scirpus juncoides, Cyperus difformis, Monochoria vaginalis, Alisma canaliculatum* and the like, and they also exhibit significant activities against recently problemed perennial weeds such as *Cyperus serotinus, Sagittaria pygmaea* in pre- and post-emergence treatments. Further, when they are used for an upland field, they show effects in the pre-emergence treatment before the generation of the weeds, or in the post-emergence treatment at the germination stage. As is mentioned above, the compounds according to the present invention have wide herbicidal spectra.

The compounds according to the present invention are useful as herbicides for the weeds generated in various grains, vegetables, orchards, turfs, pastures, tea plantations, mulberry plantations, rubber plantations, forests and non-cultivated fields as well as that generated in paddy fields.

In Japanese Provisional Patent Publications No. 44543/1978 and No. 27535/1979, compounds consisting of an N-substituted benzenesulfonamide type and N-substituted-N-benzoylbenzenesulfonamide type having herbicidal effects were disclosed. However, the herbicidal effects of the compounds according to the present invention are superior to that of the known compounds (see the experiments hereinafter). Particularly, the compounds according to the present invention have excellent properties in that herbicidal effects against the annual weeds and the perennial weeds in a paddy field are significantly high and phytotoxicity on rice plants is low.

The compounds according to the present invention can be produced according to any one of the reaction processes shown in FIG. 1. In FIG. 1 $R^1$ and $R^2$ have the same meanings as defined above and X and Y each represent a halogen atom.

PROCESS 1 (A - B)

A benzenesulfonyl chloride derivative of the general formula (2) is reacted with propargylamine to obtain an N-propargylbenzenesulfonamide derivative of the general formula (4). A compound of the general formula (4) is reacted with 2-trifluoromethylbenzoyl halide to synthesize a compound of the general formula (1).

PROCESS 2 (C - B)

A benzenesulfonamide derivative of the general formula (3) are reacted with propargyl halide to obtain a compound of the general formula (4). The compound of the general formula (4) is reacted with 2-trifluoromethylbenzoyl halide to obtain a compound of the general formula (1).

PROCESS 3 (D - E)

A compound of the general formula (3) is reacted with 2-trifluoromethylbenzoyl halide to obtain an N-(2-trifluoromethylbenzoyl)-benzenesulfonamide derivative. A compound of the general formula (5) is reacted with propargyl halide to synthesize a compound of the general formula (1).

In each of reaction processes of A, B, C, D and E, a base is employed. As the base to be used, there may be mentioned alkali metal or alkaline earth metal hydroxides such as sodium hydroxide, potassium hydroxide, calcium hydroxide, etc.; alkali metal carbonates such as sodium carbonate, potassium carbonate, etc.; inorganic bases of an alkali metal such as lithium hydride, sodium hydride, potassium hydride, etc.; as well as amines such as trimethylamine, triethylamine, pyridine, etc.

For carrying out the each reaction of A, B, C, D and E, a solvent may preferably be used. As the solvent, there may be mentioned ketones such as acetone, methyl ethyl ketone, etc.; esters such as methyl acetate, ethyl acetate, etc.; hydrocarbon series solvents such as hexane, benzene, toluene, etc.; halogen series solvents such as chloroform, dichloromethane, carbon tetrachloride, etc.; aprotic solvents such as dimethylformamide, dimethylsulfoxide, hexamethylphosphortriamide, etc.; and ethers such as diethyl ether, dimethoxyethane, tetrahydrofuran, etc.

Each reaction of A, B, C and D smoothly proceeds at 0° C. or a reflux temperature of the solvent.

When the compound of the present invention is used as the herbicide, the obtained compound itself may be used. Further, when the compound is used by formulation such as granules, wettable powders, dusts, emulsifiable concentrates, fine granules, flowable suspension and the like, better results can be obtained. For preparation of herbicidal compositions having such formulations, solid carriers such as talc, bentonite, clay, kaolin, diatomaceous earth, white carbon, vermiculite, slack lime, siliceous sand, ammonium sulfate, urea and the like; liquid carriers such as alcohols, dioxane, acetone, cyclohexanone, methylnaphthalene, dimethylformamide and the like; emulsifiers such as alkyl sulfates, alkyl sulfonates, polyoxyethylene glycohol ether, polyoxyethylene alkyl aryl ether polyoxyethylene sorbitan monoalkylates and the like; and various additives such as emulsifier, dispersants, carboxymethylcellulose, gum arabic and the like are formulated, and then homogeneously mixed or dissolved with the compound of the present invention.

Now, formulating examples will be explained in the following. However, the kinds and formulating ratios of the additives would not be restricted to them and could be modified in the various ranges. Numerical numbers represent weight percents.

Formulating Example 1

WETTABLE POWDER

| | |
|---|---|
| Compound of the present invention | 30% |
| Sodium salt of the higher alcohol sulfate ester | 5% |
| Clay | 65% |

The above compounds are homogeneously ground under mixing to form wettable powder.

Formulating Example 2

EMULSIFIABLE CONCENTRATE

| | |
|---|---|
| Compound of the present invention | 20% |
| Polyoxyethylene alkyl aryl ether | 10% |
| Isophorone | 50% |
| Xylene | 20% |

The above compounds are homogeneously dissolved to form an emulsifiable concentrate.

Formulating Example 3

GRANULES

| | |
|---|---|
| Compound of the present invention | 3% |
| Bentonite | 40% |
| Clay | 50% |
| Sodium lignosulfonate | 7% |

The above compounds are homogeneously ground under mixing, milled by adding water, and then granulated and dried to be a granules.

Formulating Example 4

DUST

| | |
|---|---|
| Compound of the present invention | 3% |
| Clay | 97% |

The above compounds are homogeneouslyl ground under mixing to form a dust.

The components according to the present invention are intended to improve the effects as herbicides and can be used mixed with other herbicides, and optionally synergistic effects with other herbicides can be expected. For these examples, following herbicides can be exemplified.

(1) Herbicides of diphenyl ether type
2,4-Dichlorophenyl-4'-nitrophenyl ether;
2,4,6-Trichlorophenyl-4'-nitrophenyl ether;
2-Chloro-4-trifluoromethylphenyl-3'-ethoxy-4'-nitrophenyl ether;
2,4-Dichlorophenyl-4'-nitro-3'-methoxyphenyl ether;
2,4-Dichlorophenyl-3'-methoxycarbonyl-4'-nitrophenyl ether.

(2) Herbicides of phenoxy type
2,4-Dichlorophenoxyacetic acid;
2-Methyl-4-chlorophenoxybutyric acid;
2-Methyl-4-chlorophenoxyacetic acid (including esters and salts thereof).

(3) Herbicides of triazine type
2-Chloro-4,6-bisethylamino-1,3,5-triazine;
2-Chloro-4-ethylamino-6-isopropylamino-1,3,5-triazine;
2-Methylthio-4,6-bisethylamino-1,3,5-triazine;
2-Methylthio-4,6-bisisopropylamino-1,3,5-triazine.

(4) Herbicides of urea type
3-(3,4-Dichlorophenyl)-1,1-dimethylurea;
3 -(3,4-Dichlorophenyl)-methoxy-1-methylurea;
1-(2,2-Dimethylbenzyl)-3-p-tolylurea.

(5) Herbicides of carbamate type
Isopropyl-N-(3-chlorophenyl)carbamate;
Methyl-N-(3,4-dichlorophenyl)carbamate.

(6) Herbicides of acid anilide type
3,4-Dichloropropionanilide;
N-methoxymethyl-2,6-diethyl-α-chloroacetanilide;
2-Chloro-2', 6'-diethyl-N-(butoxymethyl)acetanilide;
2-Chloro-2', 6'-diethyl-N-(n-propoxyethyl)acetanilide;
N-chloroacetyl-N-(2,6-diethylphenyl)-glycine ethyl ester (7) Herbicides of thiol carbamate type
S-(4-chlorobenzyl)-N,N-diethylthiol carbamate;
S-ethyl-N,N-hexamethylenethiol carbamate.

(8) Herbicides of uracil type
5-Bromo-3-sec-butyl-6-methyluracil;
3-Cyclohexyl-5,6-trimethyleneuracil.

(9) Herbicdes of pyridinium chloride type
1,1'-Dimethyl-4,4-bispyridinium chloride.

(10) Herbicides of phosphorus type
N,N-bis(phosphonomethyl)-glycine;
0-ethyl-O-(2-nitro-5-methylphenyl)-N-sec-butylphosphoramide thioate;
S-(2-methyl-1-piperidylcarbonylmethyl)-O,O-di-n-propyldithiophosphate;
S-(2-methyl-1-piperidylcarbonylmethyl)-O,O-diphenyldithiophosphate.

(11) Herbicides of toluidine type
α, α, α-Trifluoro-2,6-dinitro-N,N-dipropyl-p-toluidine.

(12) Other type herbicides
5-tert-Butyl-3-(2,4-dichloro-5-isopropoxyphenyl)-1,3,4-oxadiazoline-2-one;
3-Isopropyl-1H-2,1,3-benzothiadiazine-(4)-3H-one-2,2-dioxide;
α-(β-Naphthoxy)-propionanilide;
4-(2,4-Dichlorobenzoyl)-1,3-dimethylpyrazol-5-yl p-toluene sulfonate.

However, formulations are not restricted to thereabove.

Furthermore, the compounds according to the present invention can be used together with insecticides, nematicides, plant growth regulators and fertilizers, if necessary.

The present invention will be explained in more detail by referring Examples.

EXAMPLE 1

(1)

[Structure: 3-chlorobenzenesulfonyl chloride] —SO$_2$Cl + H$_2$NCH$_2$C≡CH ⟶

[Structure: N-propargyl-3-chlorobenzenesulfonamide] —SO$_2$NHCH$_2$C≡CH

Sodium hydroxide (0.60 g, 15 mmol) was dissolved in 10 ml of water and this solution was added to 0.66 g of propargylamine (12 mmol). Under ice-cooling, 2.11 g of 3-chlorobenzenesulfonyl chloride (10 mmol) was added dropwise to the mixture. The reaction temperature was raised again to room temperature and the mixture was stirred for 3 hours. The reaction mixture was extracted with ethyl acetate, dried over anhydrous magnesium sulfate, and concentrated to obtain N-propargyl-3-chlorobenzenesulfonamide (2.20 g). NMR spectrum of this product was as follows.

NMR (CDCl$_3$): δ 2.10 (t, J=3 Hz, 1H), 3.83 (bs, 2H), 5.10 (bs, 1H), 7.13–7.77 (m, 4H).

(2)

[Structure] —SO$_2$NHCH$_2$C≡CH + [Structure with CF$_3$] —COCl ⟶

[Product structure with CH$_2$C≡CH, SO$_2$N, C=O, CF$_3$, Cl]

After being washed with n-hexane, 50% sodium hydride in oil (0.24 g, 5 mmol) was suspended in dried THF (20 ml). To the suspension was added dropwise a solution of 1.15 g of N-propargyl-3-chlorobenzenesulfonamide (5 mmol) dissolved in THF. The mixture was stirred for an hour at room temperature to prepare sodium salt thereof. To the solution was added dropwise 1.04 g of 2-trifluoromethylbenzoyl chloride (5 mmol) dissolved in THF and then the mixture was stirred for 2 hours at room temperature. After THF was evaporated under reduced pressure and an aqueous ammonium chloride solution was added, the reaction mixture was extracted with ethyl acetate and dried over anhydrous magnesium sulfate. The crude products were purified through a column chromatography (silica gel, ethyl acetate:n-hexane =3:7) to obtain colorless crystals of N-propargyl-N-2-trifluoromethylbenzoyl-3-chlorobenzene-sulfonamide (1.50 g, Yield: 74%.

Melting point: 111°–114° C.

IR (KBr): 3300, 1690, 1365, 1320, 1180, 1170 cm$^{-1}$

NMR (CDCl$_3$): δ 2.30 (t, J=3 Hz, 1H), 4.50 (d, J=3 Hz, 2H), 7.27–7.97 (m, 8H).

Mass (m/e): 403 (M$^+$+2), 401 (M$^+$), 210, 173, 145, 111.

Elementary Analysis: C$_{17}$H$_{11}$ClF$_3$NO$_3$S calculated: C, 50.82; H, 2.76; N, 3.49; found: C, 50.17; H, 2.81; N, 3.92.

EXAMPLE 2

(1)

[Structure: 3-methylbenzenesulfonyl chloride with CH$_3$] —SO$_2$Cl + H$_2$NCH$_2$C≡CH ⟶

[Structure with CH$_3$] —SO$_2$NHCH$_2$C≡CH

Sodium hydroxide (0.60 g, 15 mmol) was dissolved in 10 ml of water and 0.66 g of propargylamine (12 mmol) was added thereto. Under ice-cooling, 1.91 g of 3-methylbenzenesulfonyl chloride (10 mmol) was added dropwise to the solution. The reaction temperature was raised again to room temperature and the mixture was stirred for 3 hours. The reaction mixture was extracted with ethyl acetate, dried over anhydrous magnesium sulfate and concentrated to obtain N-propargyl-3-methylbenzenesulfonamide (2.17 g). NMR spectrum of this product was as follows.

NMR (CDCl$_3$): δ2.12 (t, J=3 Hz, 1H), 2.43 (s, 3H), 3.88 (d, J=3 Hz, 2H), 5.33 (bs, 1H), 7.28–7.78 (m, 4H).

(2)

[Structure with CH$_3$] —SO$_2$NHCH$_2$C≡CH + [Structure with CF$_3$] —COCl ⟶

[Product structure with CH$_3$, SO$_2$N, CH$_2$C≡CH, C=O, CF$_3$]

After being washed with n-hexane, 0.24 g of 50% sodium hydride in oil (5 mmol) was suspended in dried THF (20 ml). To the suspension was added dropwise 1.05 g of N-propargyl-3-methylbenzenesulfonamide (5 mmol) dissolved in THF and the mixture was stirred for an hour at room temperature to form sodium salt of N-propargyl-3-methylbenzenesulfonamide. To this solution was added dropwise a THF solution containing 2-trifluoromethylbenzoyl chloride (1.04 g, 5 mmol) was the mixture was stirred for two hours at room temperature. After THF was evaporated under reduced pressure and an aqueous ammonium chloride solution was added thereto, the reaction mixture was extracted with ethyl acetate and dried over anhydrous magnesium sulfate. The crude products were purified through column chromatography (silica gel, ethyl acetate:n-hexane=3:7) to obtain 1.32 g of N-propargyl-N-(2-trifluoromethylbenzoyl)-3-methylbenzenesulfonamide (Yield: 69%) as colorless crystals.

Melting point: 81°–85° C.

IR (KBr): 3300, 1685, 1360, 1320, 1165, 1090, 720 cm$^{-1}$.

NMR (CDCl$_3$): δ2.25 (t, J=3 Hz, 1H), 2.33 (s, 3H), 4.48 (d, J=3 Hz, 2H), 7.20–7.83 (m, 8H).

Mass (m/e): 381 (M+), 210, 173, 145, 91.

Elementary Analysis: C$_{18}$H$_{14}$F$_3$NO$_3$S
calculated: C, 56.69; H, 3.70; N, 3.67; found: C, 56.60; H, 3.64; N, 3.63.

EXAMPLES 3–18

According to the same procedures as in the above Example 1, compounds having physical properties shown in the following Tables 1 and 2 were obtained. Incidentally, structures and melting points of the resulting compounds are shown in Table 1 and NMR values of these compounds are shown in Table 2. As the solvent for measurement of the NMR values, CDCl$_3$ was used. Chemical shifts were shown by δ values.

TABLE 1

| Example No. | Structure (in the above formula (1)) R$^1$ | R$^2$ | Melting point (°C.) |
|---|---|---|---|
| 3 | 3-CF$_3$ | H | 53.5–54.5 |
| 4 | 3-F | H | 68–69 |
| 5 | 3-Br | H | 125–126 |
| 6 | 3-Cl | 5-Cl | 94.5–96.5 |
| 7 | 3-Cl | 6-Cl | 142.5–143.5 |
| 8 | 3-Cl | 4-Cl | 85.5–87.5 |
| 9 | 3-Cl | 4-Me | 91–93 |
| 10 | 3-NO$_2$ | H | 141–143 |
| 11 | 3-CN | H | 125–127 |
| 12 | 3-MeO | H | 110–111 |
| 13 | 3-MeO | 4-MeO | Viscous oil |
| 14 | 3-CO$_2$Me | H | 103–110 |
| 15 | 3-I | H | 105–106 |
| 16 | 3-Me | 6-Me | 92–93 |
| 17 | 3-Me | 4-Me | 90–91 |
| 18 | 3-Cl | 2-Me | 104.5–105.5 |
| Compared compound (2) | H | H | 74 |
| Compared compound (3) | H | 4-Me | 65 |

TABLE 2

| Example No. | NMR measured value |
|---|---|
| 3 | 2.30 (t, J = 3Hz, 1H), 4.49 (d, J = 3Hz, 2H), 7.2–8.5 (m, 8H) |
| 4 | 2.31 (t, J = 3Hz, 1H), 4.49 (d, J = 3Hz, 2H), 7.15–7.86 (m, 8H) |
| 5 | 2.31 (t, J = 3Hz, 1H), 4.5 (d, J = 3Hz, 2H), 7.13–8.03 (m, 8H) |
| 6 | 2.35 (t, J = 3Hz, 1H), 4.49 (d, J = 3Hz, 2H), 7.2–7.9 (m, 7H) |
| 7 | 2.36 (t, J = 3Hz, 1H), 4.57 (d, J = 3Hz, 2H), 7.15–7.93 (m, 7H) |
| 8 | 2.33 (t, J = 3Hz, 1H), 4.47 (d, J = 3Hz, 2H) |
| 9 | 2.30 (t, J = 3Hz, 1H), 2.43 (s, 3H), 4.49 (d, J = 3Hz, 2H), 7.2–7.83 (m, 7H) |
| 10 | 2.40 (t, J = 3Hz, 1H), 4.49 (d, J = 3Hz, 2H), 7.2–7.66 (m, 4H), 7.71 (t, J = 8Hz, 1H), 8.24–8.55 (m, 2H), 8.8 (t, J = 2Hz, 1H) |
| 11 | 2.36 (t, J = 3Hz, 1H), 4.46 (d, J = 3Hz, 2H), 7.2–8.4 (m, 8H) |
| 12 | 2.29 (t, J = 3Hz, 1H), 3.79 (s, 3H), 4.53 (d, J = 3Hz, 2H), 6.93–7.7 (m, 8H) |
| 13 | 2.31 (t, J = 3Hz, 1H), 3.81 (s, 3H), 3.86 (s, 3H), 4.48 (d, J = 3Hz, 2H), 7.2–7.7 (m, 7H) |
| 14 | 2.35 (t, J = 3Hz, 1H), 3.91 (s, 3H), 4.51 (d, J = 3Hz, 2H), 7.2–8.6 (m, 8H) |
| 15 | 2.33 (t, J = 3Hz, 1H), 4.51 (d, J = 3Hz, 2H), 7.15–8.2 (m, 8H) |
| 16 | 2.20 (s, 3H), 2.30 (t, J = 3Hz, 1H), 2.50 (s, 3H), 4.56 (d, J = 3Hz, 2H), 7.0–7.53 (m, 7H) |
| 17 | 2.23 (t, J = 3Hz, 1H), 2.25 (s, 3H), 2.28 (s, 3H), 4.49 (d, J = 3Hz, 2H), 7.06–7.66 (m, 7H) |
| 18 | 2.32 (t, J = 3Hz, 1H), 2.63 (s, 3H), 4.52 (d, J = 3Hz, 2H), 7.0–7.8 (m, 7H) |
| Compared compound (2) | 2.30 (t, J = 3Hz, 1H), 4.51 (s, 3H), 7.13–8.28 (m, 5H) |
| Compared compound (3) | 2.30 (t, J = 3Hz, 1H), 2.43 (s, 3H), 4.48 (d, J = 3Hz, 2H), 7.18–8.08 (m, 5H) |

EXPERIMENT 1

Pot test for paddy field weeds at early germination stages

Wagner's pots were packed with "KIKUKAWA" paddy soil. After pouring water, dressing and plowing, the pots were filled with water, to a depth of 3 cm and each seed of *Scirpus juncoides*, Barnyardgrass (*Echinochloa oryzicola*), smallflower umbrellaplant (*Cyperus difformis*) and *Monochoria vaginalis* was planted. Next day the determined amount of each sample (10%) prepared according to the method of Formulating Example 1 was added dropwise to the surface of flooding water as an active ingredient so as to be 0.5, 1, and 4 kg per hectare. Test samples were kept in greenhouse and after 3 weeks herbicidal effect was evaluated. The results were shown in table 3.

The results were evaluated by indexes as follows.

| Herbicidal activity | |
|---|---|
| Index | Meanings |
| 5 | Complete killing |
| 4 | Great herbicidal effect |
| 3 | Medium herbicidal effect |
| 2 | Little herbicidal effect |
| 1 | Minute herbicidal effect |
| 0 | No effect |

The Compared compound (1) is exemplified in Japanese Provisional Patent Publication No. 27535/1979 and compared compounds (2) and (3) were those synthesized for comparison according to the method of the present Examples at this time. Namely, Comparative compound (1) is

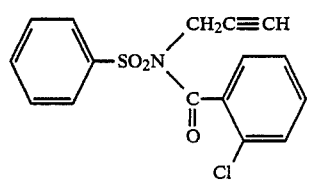

Comparative compound (2) is

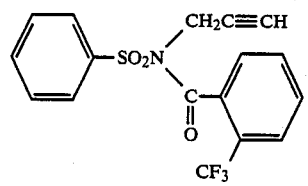

and Comparative compound (3) is

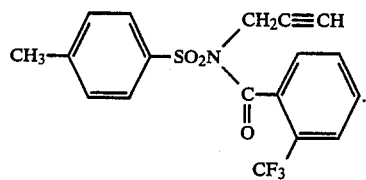

TABLE 3

| Example No. | Dosage ai kg/HA | Herbicidal activity |||| 
|---|---|---|---|---|---|
| | | Echinochloa oryzicola | Cyperus difformis | Monochoria vaginalis | Scirpus juncoides |
| 1 | 4 | 5 | 5 | 5 | 5 |
|  | 1 | 5 | 5 | 5 | 5 |
|  | 0.5 | 5 | 5 | 5 | 5 |
| 2 | 4 | 5 | 5 | 5 | 5 |
|  | 1 | 5 | 5 | 5 | 5 |
|  | 0.5 | 5 | 5 | 5 | 5 |
| 3 | 4 | 5 | 5 | 5 | 5 |
|  | 1 | 5 | 5 | 5 | 5 |
| 4 | 4 | 5 | 5 | 5 | 5 |
|  | 1 | 5 | 5 | 5 | 5 |
| 5 | 4 | 5 | 5 | 4 | 5 |
|  | 1 | 5 | 5 | 3 | 5 |
| 6 | 4 | 5 | 5 | 5 | 5 |
|  | 1 | 5 | 5 | 5 | 5 |
| 7 | 4 | 5 | 3 | 0 | 1 |
|  | 1 | 5 | 2 | 0 | 0 |
| 8 | 4 | 5 | 5 | 1 | 2 |
|  | 1 | 5 | 5 | 0 | 0 |
| 9 | 4 | 5 | 5 | 5 | 4 |
|  | 1 | 5 | 5 | 2 | 4 |
| 10 | 4 | 5 | 5 | 4 | 4 |
|  | 1 | 5 | 5 | 2 | 4 |
| 11 | 4 | 5 | 5 | 5 | 5 |
|  | 1 | 5 | 5 | 5 | 5 |
| 12 | 4 | 5 | 5 | 5 | 5 |
|  | 1 | 5 | 5 | 5 | 5 |
| 13 | 4 | 5 | 5 | 5 | 5 |
|  | 1 | 5 | 5 | 2 | 4 |
| 14 | 4 | 4 | 3 | 0 | 4 |
|  | 1 | 3 | 2 | 0 | 1 |
| 15 | 4 | 5 | 5 | 5 | 5 |
|  | 1 | 5 | 5 | 1 | 3 |
| Compared compound (1) | 4 | 5 | 5 | 5 | 3 |
|  | 1 | 5 | 3 | 1 | 0 |
|  | 0.5 | 4 | 2 | 0 | 0 |
| Compared compound (2) | 4 | 5 | 5 | 5 | 5 |
|  | 1 | 5 | 4 | 2 | 4 |
|  | 0.5 | 5 | 5 | 2 | 5 |
| Compared compound (3) | 4 | 5 | 2 | 0 | 0 |
|  | 1 | 5 | 1 | 0 | 0 |
|  | 0.5 | 5 | 3 | 1 | 0 |

EXPERIMENT 2

Phytotoxicity test on transplanted seedling of paddy field

Wagner pots were packed with "KIKUKAWA" paddy soil. After pouring water, fertilizing and plowing, the pots were filled with water to a depth of 3 cm and seeds of Barnyardgrass (*Echinochloa oryzicola*) were planted. Seedlings of rice at 2 leaf stage were transplanted at a depth of 2 cm into the soil. At a day after transplantation, the determined amount of the each sample (10% by weight) prepared according to the method of Formulating Example 1 was added dropwise. Test samples were kept in a greenhouse and herbicidal effects and phytotoxicity were investigated for 3 weeks after treatment with the herbicide. The results were shown in Table 4.

The results were evaluated by indexes as follows.

| Herbicidal activity and phytotoxicity ||
|---|---|
| Index | Meanings |
| 5 | Complete killing |
| 4 | Great herbicidal effect (damage) |
| 3 | Medium herbicidal effect (damage) |
| 2 | Little herbicidal effect (damage) |
| 1 | Minute herbicidal effect (damage) |
| 0 | No effect (No damage) |

TABLE 4

| Example No. | Dosage ai kg/HA | Phytotoxicity in paddy field Transplanted rice | Herbicidal activity Barnyardgrass at germination |
|---|---|---|---|
| 1 | 4 | 0 | 5 |
|  | 1 | 0 | 5 |
| 2 | 4 | 0 | 5 |
|  | 1 | 0 | 5 |
| 3 | 4 | 0 | 5 |
|  | 1 | 0 | 5 |
| 4 | 4 | 4 | 5 |
|  | 1 | 1 | 5 |
| 5 | 4 | 1 | 5 |
|  | 1 | 0 | 5 |
| 6 | 4 | 1 | 5 |
|  | 1 | 0 | 5 |
| 8 | 4 | 0 | 5 |
|  | 1 | 0 | 5 |
| 9 | 4 | 1 | 5 |
|  | 1 | 1 | 5 |
| 11 | 4 | 2 | 5 |
|  | 1 | 1 | 5 |
| 12 | 4 | 1 | 5 |
|  | 1 | 1 | 5 |
| 13 | 4 | 3 | 5 |
|  | 1 | 2 | 5 |

We claim:

1. An N-propargyl-N-(2-trifluoromethylbenzoyl)-3-substituted benzenesulfonamide represented by the general formula:

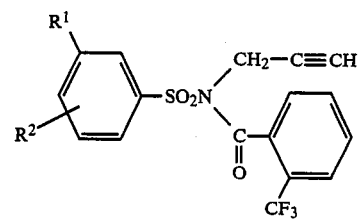

wherein $R^1$ represents a halogen atom, a lower alkyl group, a lower alkoxy group, a perfluoro-lower alkyl group having 1 to 4 carbon atoms, a nitro group, a cyano group, a carboxyl group or a lower alkoxycarbonyl group; and $R^2$ represents a hydrogen atom, a halogen atom, a lower alkyl group, a perfluoro-lower alkyl group having 1 to 4 carbon atoms, a lower alkoxy group, a nitro group, a cyano group, a carboxyl group or a lower alkoxycarbonyl group.

2. An N-propargyl-N-(2-trifluoromethylbenzoyl)-3-substituted benzenesulfonamide according to claim 1, wherein $R^1$ represents a halogen atom, a methyl group, a methoxy group, a perfluoro-methyl group, a nitro group, a cyano group, or a methoxycarbonyl group; and $R^2$ represents a hydrogen atom, a chlorine atom, or a methyl group.

3. An N-propargyl-N-(2-trifluoromethylbenzoyl)-3-substituted benzenesulfonamide according to claim 2, wherein said compound is selected from the group consisting of N-propargyl-N-(2-trifluoromethylbenzoyl)-3-fluorobenezenesulfonamide, N-propargyl-N-(2 trifluoromethylbenzoy)-3,5-dichlorobenzenesulfonamide, N-propargyl-N-(2-trifluoromethylbenzoyl)-3-chlorobenzenesulfonamide, N-propargyl-N-(2-trifluoromethylbenzoyl)-3-cyanobenzenesulfonamide, N-propargyl-N-(2-trifluoromethylbenzoyl)-3-methylbenzenesulfonamide, N-propargyl-N-(2-trifluoromethylbenzoyl)-3-trifluoromethylbenzenesulfonamide, N-propargyl-N-(2-trifluoromethylbenzoyl)-3-methoxybenzenesulfonamide, N-propargyl-N-(2-trifluoromethylbenzoyl)-3-chloro-4-methylbenzenesulfonamide, N-propargyl-N-(2-trifluoromethylbenzoyl)-2-methyl-3-chlorobenzenesulfonamide, N-propargyl-N-(2-trifluoromethylbenzoyl)-3-iodobenzenesulfonamide, N-propargyl-N-(2-trifluoromethylbenzoyl)-3-bromobenzenesulfonamide, N-propargyl-N-(2-trifluoromethylbenzoyl)-3,4-dichlorobenzenesulfonamide, N-propargyl-N-(2-trifluoromethylbenzoyl)-3,4-dimethoxybenzenesulfonamide and N-propargyl-N-(2-trifluoromethylbenzoyl)-3,4-dimethylbenzenesulfonamide.

4. A selective herbicide containing an N-propargyl-N-(2-trifluoromethylbenzoyl)-3-substituted benzenesulfonamide represented by the general formula:

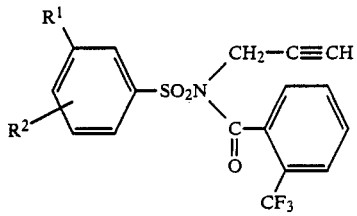

wherein $R^1$ represents a halogen atom, a lower alkyl group, a lower alkoxy group, a perfluoro-lower alkyl group having 1 to 4 carbon atoms, a nitro group, a cyano group, a carboxyl group or a lower alkoxycarbonyl group; and $R^2$ represents a hydrogen atom, a halogen atom, a lower alkyl group, a perfluoro-lower alkyl group having 1 to 4 carbon atoms, a lower alkoxy group, a nitro group, a cyano group, a carboxyl group or a lower alkoxycarbonyl group, as an active ingredient.

5. A selective herbicide according to claim 4, wherein $R^1$ represents a halogen atom, a methyl group, a methoxy group, a perfluoro-methyl group, a nitro group, a cyano group, or a methoxycarbonyl group; and $R_2$ represents a hydrogen atom, a chlorine atom, or a methyl group.

6. A selective herbicide according to claim 5, wherein said N-propargyl-N-(2-trifluoromethylbenzoyl)-3-substituted benzenesulfonamide is selected from the group consisting of N-propargyl-N-(2-trifluoromethylbenzoyl)-3-fluorobenezenesulfonamide, N-propargyl-N-(2-trifluoromethylbenzoyl)-3,5-dichlorobenzenesulfonamide, N-propargyl-N-(2-trifluoromethylbenzoyl)-3-chlorobenzenesulfonamide, N-propargyl-N-(2-trifluoromethylbenzoyl)-3-cyanobenzenesulfonamide, N-propargyl-N-(2-trifluoromethylbenzoyl)-3-methylbenzenesulfonamide, N-propargyl-N-(2-trifluoromethylbenzoyl)-3-trifluoromethylbenzenesulfonamide, N-propargyl-N-(2-trifluoromethylbenzoyl)-3-methoxybenzenesulfonamide, N-propargyl-N-(2-trifluoromethylbenzoyl)-3-chloro-4-methylbenzenesulfonamide, N-propargyl-N-(2-trifluoromethylbenzoyl)-2-methyl-3-chlorobenzenesulfonamide, N-propargyl-N-(2-trifluoromethylbenzoyl)-3-iodobenzenesulfonamide, N-propargyl-N-(2-trifluoromethylbenzoyl)-3-bromobenzenesulfonamide, N-propargyl-N-(2-trifluoromethylbenzoyl)-3,4-dichlorobenzenesulfonamide, N-propargyl-N-(2-trifluoromethylbenzoyl)-3,4-dimethoxybenzenesulfonamide and N-propargyl-N-(2-trifluoromethylbenzoyl)-3,4-dimethylbenzenesulfonamide.

* * * * *